US00PP17307P2

(12) United States Plant Patent
Larsen

(10) Patent No.: US PP17,307 P2
(45) Date of Patent: Dec. 26, 2006

(54) ***OSTEOSPERMUM* PLANT NAMED 'SUNNY FLORENCE'**

(50) Latin Name: *Osteospermum ecklonis (DC) T. Norl.*
Varietal Denomination: Sunny Florence

(75) Inventor: Bjarne Nyholm Larsen, Odense (DK)

(73) Assignee: Sunny Osteospermum APS, Odense (DK)

( * ) Notice: Subject to any disclaimer, the term of this patent is extended or adjusted under 35 U.S.C. 154(b) by 0 days.

(21) Appl. No.: 11/234,151

(22) Filed: Sep. 26, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner LLP

(57) ABSTRACT

A new distinct cultivar of *Osteospermum* plant named 'Sunny Florence', characterized by strikingly clear orange ray florets, RHS 29C (upper side); gray-purple disc florets (RHS 186A (tip) to light purple, RHS 76D (base)) when inflorescence opens; many ray florets (35) in 1½ whorl; gray-green young foliage, RHS 189 A; and narrow leaves with 8 distinct pointed lobes.

3 Drawing Sheets

Botanical designation: *Osteospermum ecklonis* (*DC*) *T. Norl.*
Variety denomination: 'Sunny Florence'.

BACKGROUND OF THE INVENTION

The present invention relates to a new and distinct cultivar of *Osteospermum* plant, botanically known as *Osteospermum ecklonis* (*DC*) *T. Norl.,* commonly known as Cape Daisy, and hereinafter referred to by the variety denomination 'Sunny Florence'.

The new *Osteospermum* is a product of a planned breeding program conducted by the Inventor, Bjarne Larsen, in Stige, Odense, Denmark. The objective of the breeding program was to develop a new *Osteospermum* cultivar with upright, compact plant habit, interesting inflorescence color, good branching performance, low growth retardant requirements, and low temperature tolerance.

The new *Osteospermum* originated from a planned crossing of two selected *Osteospermum* parent plants made by the Inventor in 2003 in Stige, Odense, Denmark. The female or seed parent is an *Osteospermum ecklonis* (*DC*) *T. Norl.* cultivar designated '1.154.93' (unpatented). The male or pollen parent is an *Osteospermum ecklonis* (*DC*) *T. Norl.* cultivar designated '998' (unpatented). The new *Osteospermum* cultivar 'Sunny Florence' was selected by the Inventor as a single flowering plant within the progeny of the above crossing in 2003 in a controlled environment in Stige, Odense, Denmark.

Asexual reproduction of the new *Osteospermum* cultivar by apical stem cuttings was first performed in June of 2003 in Stige, Odense, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'Sunny Florence'. These characteristics in combination distinguish 'Sunny Florence' as a new and distinct cultivar;

1. Strikingly clear orange ray florets, RHS 29C (upper side) when opening;
2. Gray-purple disc florets, when opening, (RHS 186A (tip) to light purple, RHS 76D (base)) when inflorescence opens;
3. Many ray florets (35) in 1½ whorl;
4. Gray-green young foliage, RHS 189 A (upper surface); and
5. Narrow leaves with 8 distinct pointed lobes.

Plants of the parental cultivar, '1.154.93' (unpatented) and '998' (unpatented) are unavailable to provide a detailed botanical comparison to plants of the new cultivar 'Sunny Florence'.

Of the many commercial cultivars known to the present Inventor, the most similar in comparison to the new *Osteospermum* cultivar 'Sunny Florence' is the *Osteospermum* cultivar 'Orange Symphony' (patented). In side-by-side comparisons conducted in Stige, Odense, Denmark, plants of 'Sunny Florence' differed from plants of 'Orange Symphony' in the characteristics described in Table 1:

| | |
|---|---|
| a-1: | $CH_2{=}CHCOOCH_2CH_2C_8F_{17}$ |
| a-2: | $CH_2{=}C(CH_3)COOCH_2CH_2C_8F_{17}$ |
| a-3: | $CH_2{=}CHCOOCH_2CH_2C_{12}F_{25}$ |
| a-4: | $CH_2{=}C(CH_3)COOCH_2CH_2C_{12}F_{25}$ |
| a-5: | $CH_2{=}CHCOOCH_2CH_2C_{10}F_{21}$ |
| a-6: | $CH_2{=}C(CH_3)COOCH_2C_{10}F_{21}$ |
| a-7: | $CH_2{=}CHCOOCH_2CH_2C_6F_{13}$ |
| a-8: | $CH_2{=}C(CH_3)COOCH_2CH_2C_6F_{13}$ |
| a-9: | $CH_2{=}CHCOOCH_2CH_2C_4F_9$ |
| a-10: | $CH_2{=}C(F)COOCH_2CH_2C_6F_{13}$ |

-continued

| | |
|---|---|
| a-11: | $CH_2{=}CHCOOCH_2(CH_2)_6CF(CF_3)_2$ |
| a-12: | $CH_2{=}CHCOOCH_2(CF_2)_6H$ |
| a-13: | $CH_2{=}CHCOOCH_2(CF_2)_6H$ |
| a-14: | $CH_2{=}C(CH_3)COOCH_2(CF_2)_8H$ |
| a-15: | $CH_2{=}CHCOOCH_2(CF_2)_{10}H$ |
| a-16: | $CH_2{=}CHCOOCH_2(CF_2)_{12}H$ |
| a-17: | $CH_2{=}CHCOOCH_2C(OH)HCH_2C_8F_{17}$ |
| a-18: | $CH_2{=}CHCOOCH_2CH_2N(C_3H_7)SO_2C_8F_{17}$ |
| a-19: | $CH_2{=}CHCOOCH_2CH_2N(C_2H_5)COC_7F_{15}$ |
| a-20: | $CH_2{=}CHCOO(CH_2)_2(CF_2)_8CF(CF_3)_2$ |
| a-21: | $CH_2{=}C(CH_2CH_2C_8F_{17})COOCH_2CH_2C_8F_{17}$ |

BRIEF DESCRIPTION OF THE PHOTOGRAPHS

The accompanying colored photographs illustrate the overall appearance of the new *Osteospermum* cultivar 'Sunny Florence' showing the colors as true as is reasonably possible with colored reproductions of this type. Colors in the photographs may differ slightly from the color values cited in the detailed botanical description which accurately describe the color of the new *Osteospermum* cultivar 'Sunny Florence'.

DETAILED BOTANICAL DESCRIPTION

Figure 1:
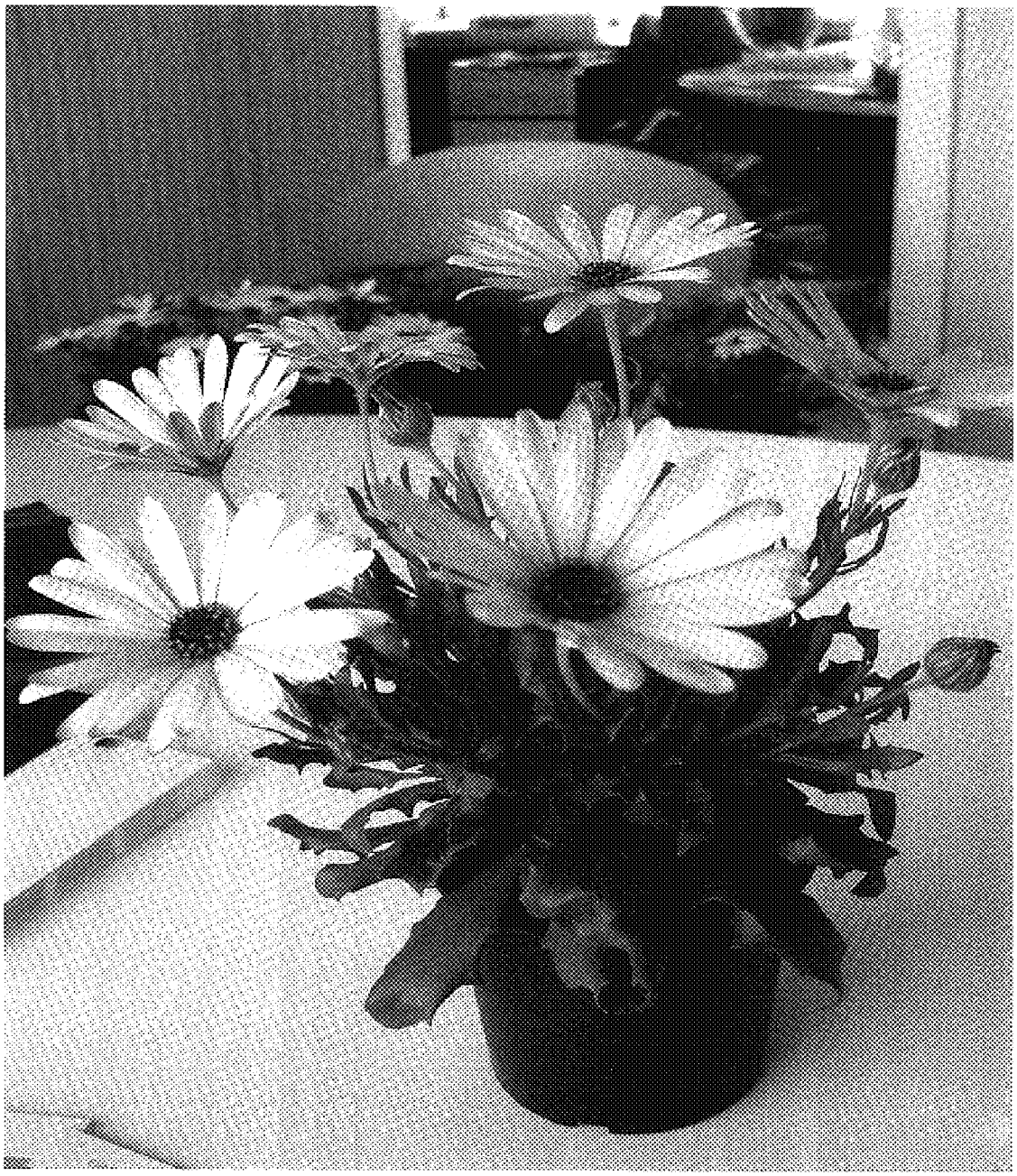
FIG. 1 shows a side perspective view of a typical potted flowering plant of 'Sunny Florence', as a produced cultivar, 20 weeks after planting.
Figure 2:
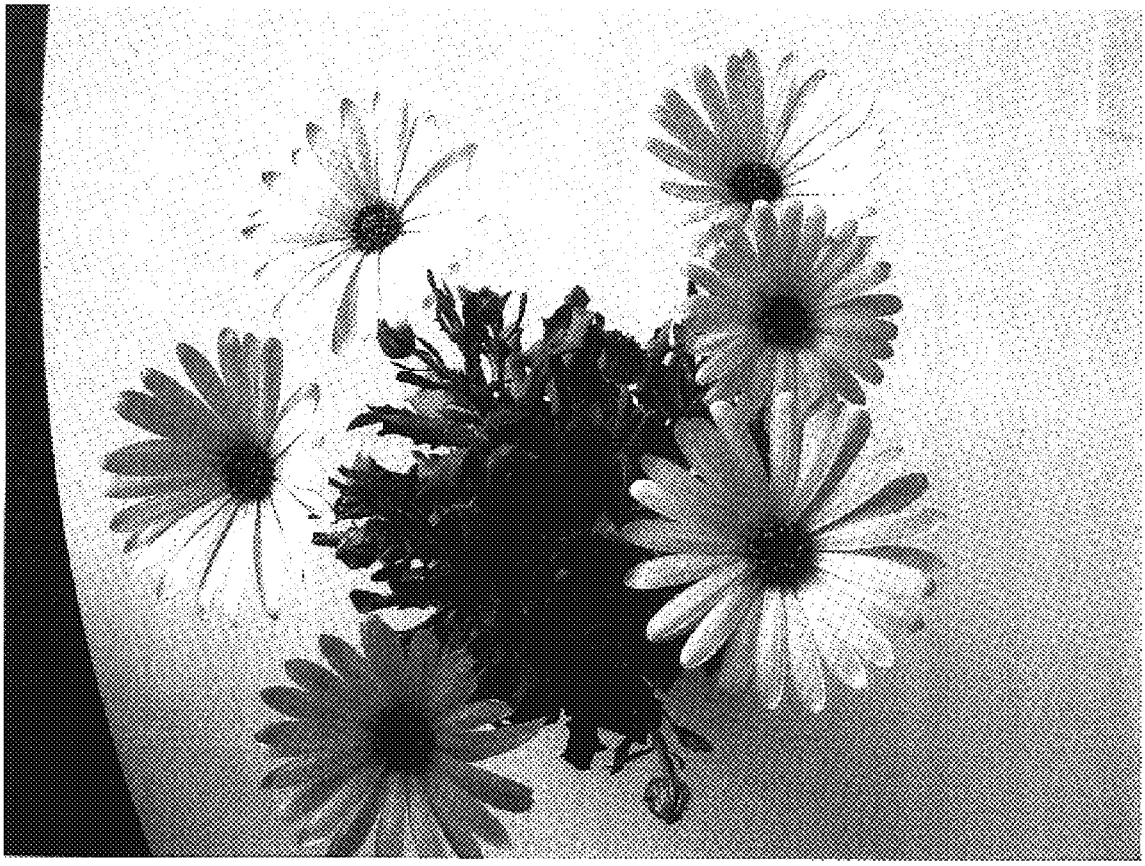
FIG. 2 shows top perspective view of a typical potted flowering plant of 'Sunny Florence', as a produced cultivar, 20 weeks after planting.
Figure 3:
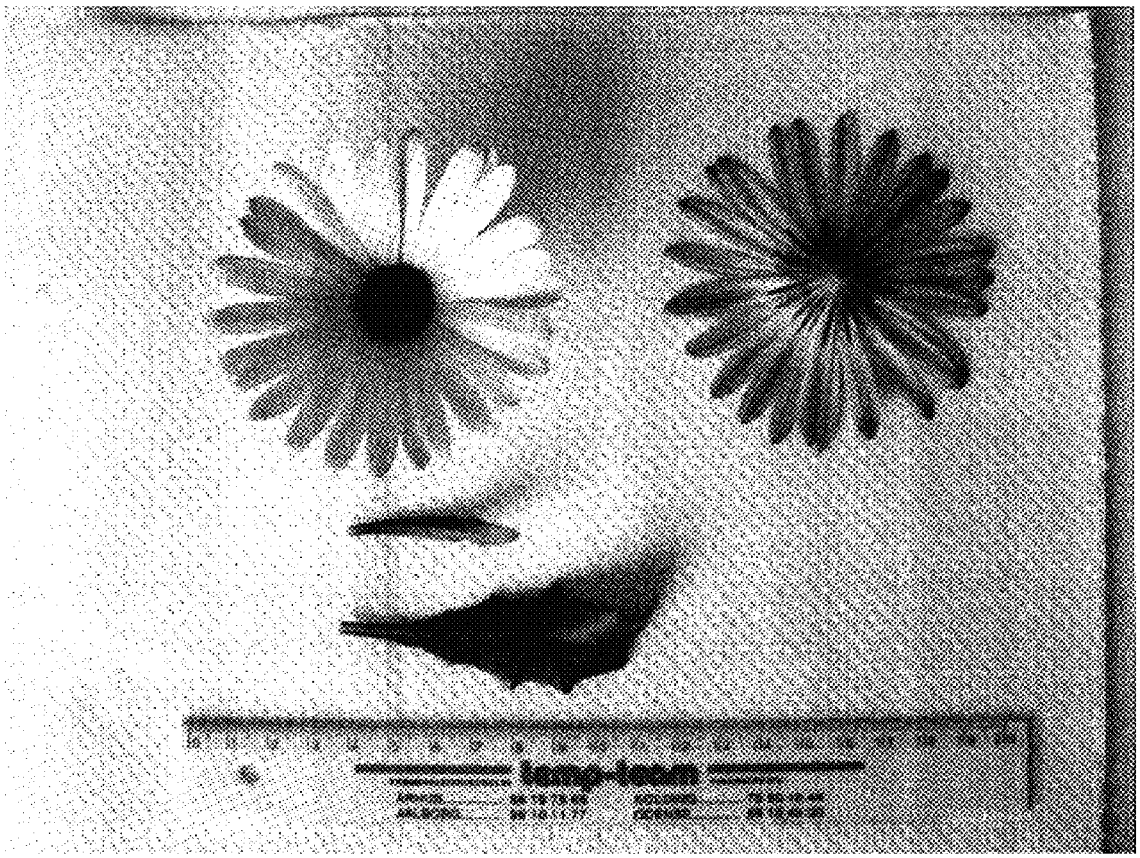
FIG. 3 shows a top and bottom view of typical leaves and inflorescences of the cultivar 'Sunny Florence', as a produced cultivar, 20 weeks after planting.

The new *Osteospermum* cultivar 'Sunny Florence' has not been observed under all possible environmental conditions. The phenotype of the new cultivar may vary with variations in environment such as temperature, light intensity, and day length, without any change in the genotype of the plant.

The aforementioned photographs, together with the following observations, measurements and values describe plants of the new *Osteospermum* cultivar 'Sunny Florence' as grown in a greenhouse and outside in Stige, Odense, Denmark, under conditions which closely approximate those generally used in commercial practice, and garden use. Vegetative propagation with apical tip cuttings (4–5 leaves) took place in a greenhouse with propagation tents for 3 weeks with the day and night temperature averaging about 20° C. day. The temperature was then lowered to the day and night temperature averaging about 14° C. The plants were subirrigated with a nutrient solution of 2–3 mS when needed and given supplementary irradiation with SON T lamps having an installed energy level of 400 $Wm^2$.

Color references are made to The Royal Horticultural Society Colour Chart (R.H.S.), $4^{th}$ edition 2000, except where general colors of ordinary significance are used. The photographs and descriptions were taken during the spring season when outdoor day temperatures ranged from 7° C. to 15° C. and outdoor night temperatures ranged from 0° C. to 7° C. The age of the plants described is 20 weeks.

Botanical classification: *Osteospermum ecklonis* (*DC*) *T. Norl.*

Parentage:

*Female or seed parent.*—*Osteospermum ecklonis* (*DC*) *T. Norl.* Designated '1.154.93' (unpatented).

*Male or pollen parent.*—*Osteospermum ecklonis* (*DC*) *T. Norl.* designated '998' (unpatented).

Propagation:

*Type.*—Apical stem cutting.

*Time and temperature to initiate roots.*—Summer: About 12 to 14 days at 20° C. to 22° C. in tunnels in a greenhouse. Winter: About 17 to 20 days at 20° C. to 22° C. in tunnels in a greenhouse.

*Time and temperature to develop roots.*—Summer: About 14 to 18 days at 20° C. to 22° C. in tunnels in a greenhouse. Winter: About 20 to 22 days at 20° C. to 22° C. in tunnels in a greenhouse.

*Rooting description.*—100% rooting.

*Rooting habit.*—Fine, fibrous and branching.

*Root color.*—White, RHS 155D.

*Root texture.*—Fine.

Plant description:

*General appearance and form.*—Perennial plant with upright, flat top plant habit and used as a bedding or potted plant. *Osteospermum* inflorescences in composite heads, daisy type.

*Growth and branching habit.*—Freely branching with lateral flowering branches forming at every node; dense and bushy.

*Growth rate/vigor.*—Vigorous.

*Plant height* (*soil level to top of plant plane*).—About 19 cm, Range 17–20 cm.

*Plant width* (*spread*).—About 17 cm, Range 15–20 cm.

*Plant strength.*—Low temperature tolerance: Withstands temperatures down to +1° C. High temperature tolerance: Up to +35° C., but flowering may cease.

*Crop time to produce a mature flowering plant.*—After rooting, about 20 weeks are required to produce flowering plants in 11 cm pots.

Branches:

*Number of branches per plant.*—8–10 primary, 26–28 secondary.

*Length.*—Primary: About 3–5 cm. Secondary: 4–12 cm (including inflorescence).

*Diameter.*—About 4–6 mm.

*Internode length.*—About 10–12 mm.

*Strength.*—Very strong.

*Aspect.*—Upright, branches angle at 45°.

*Texture.*—Glabrous.

*Color.*—Yellow-green, between RHS 144C and RHS 144D.

Foliage description:

*Arrangement.*—Alternate (5-whorl), single, lobed, oblanceolate, 8 small, triangular lobes.

*Length.*—About 3–8 cm.

*Width.*—About 1–1.5 cm.

*Overall shape of leaf.*—Oblanceolate.

*Shape at apex.*—Acute.

*Shape at base.*—Attenuate, decurrent.

*Margin.*—Entire, 8 triangular lobes.

*Texture.*—Scattered short stiff hairs along veins and edges (abaxial).

*Color of developing foliage.*—Upper surface: RHS 189A, gray-green. Lower surface: RHS 189B, gray-green.

*Color of mature foliage.*—Upper surface: RHS 137A, green. Lower surface: RHS 137C, green.

*Venation pattern.*—Brochidodromus, form of pinnate.

*Venation color.*—Not visible against background tissue.
*Petiole length.*—About 10–35 mm.
*Petiole diameter.*—About 2–4 mm (flat, winged).
*Petiole texture.*—Upper surface: Glabrous. Lower surface: Glabrous with scattered short stiff hairs.
*Petiole color.*—Upper surface: Yellow-green, RHS 144B. Lower surface: Yellow-green, RHS 144C.

Inflorescence description:
*Appearance.*—Terminal and axillary inflorescences held above and beyond the foliage. Single, composite inflorescence in daisy form, radially symmetrical, with elliptic, flat lanceolate ligulate-shaped ray florets and disc florets massed at the center; ray and disc florets arranged acropetally on a capitulum. Inflorescences face upright with aspect of 60°.
*Natural flowering season.*—Continuous throughout the spring and summer in temperate regions. Season can be extended by vernalization and long day treatments. Flowering may cease if night temperatures exceed +25° C. for several weeks.
*Time to flower.*—7 to 14 days (longevity of individual inflorescences is dependent on temperature and light conditions).
*Postproduction longevity.*—Inflorescences maintain good color and substance for about 14 days on the plant when grown in an outdoor environment. Inflorescences persistent, but wither to almost insignificance.
*Quantity of inflorescences.*—Freely flowering; more than 30 open inflorescences and inflorescence buds per plant.
*Rate of inflorescences opening.*—About 3 per week per plant, depending on light and temperature conditions.
*Fragrance.*—Flowers have a weak, fresh lemon scent.

Bud:
*Rate of opening (from showing color to fully open inflorescence).*—4 to 6 days.
*Length.*—About 0 to 20 mm at color showing.
*Diameter.*—About 0 to 12 mm.
*Shape.*—Globular until color, then ovoid.
*Color.*—From yellow-green, RHS 146C (base) to yellow, RHS 5A (apex).

Peduncle:
*Length.*—Terminal: About 7 cm. Secondary: About 6 cm. Tertiary: About 5 cm.
*Diameter.*—About 2–3 mm.
*Appearance and angle.*—Terminal: About 5 to 10 degrees from vertical. Secondary: About 30 to 45 degrees from vertical. Tertiary: About 30 to 45 degrees from vertical.
*Strength.*—Strong, stiff.
*Texture.*—Glabrous.
*Color.*—Yellow-green, RHS 144C.

Inflorescence:
*Inflorescence depth (height).*—About 6 mm.
*Inflorescence diameter.*—About 7 cm.
*Receptacle diameter.*—About 13 mm.
*Receptacle height.*—About 14 mm.
*Receptacle shape.*—Conical (inverted).
*Receptacle color.*—Yellow-green, RHS 145D.

Ray florets:
*Quantity per inflorescence.*—Typical number: 35, overlapping in 1½ whorl. Observed number: 29–38.
*Length.*—About 33 mm, Range: 32–35 mm.
*Width.*—About 7 mm.
*Overall shape.*—Elliptic, flat lanceolate, ligulate.
*Shape at apex.*—Acute with slight retuse tip.
*Shape at base.*—Cuneate.
*Margin.*—Entire.
*Texture.*—Upper surface: Velvety. Lower surface: Shiny.
*Orientation.*—Initially 20 degrees from vertical, with development, close to 0 degrees from vertical. Senescing: revolute.
*Color (when opening).*—Upper side: Orange, RHS 29C (uniform). Under side: Yellow-orange, RHS 16D, with stripes of gray-orange, RHS 165A.
*Color (when fully opened).*—Upper side: Yellow-orange, RHS 23C, with base RHS 23A. Under side: Yellow-orange, RHS 23C, with gray-red stripes, RHS 178A.

Disc florets:
*Quantity per inflorescence.*—Typical number: 80. Observed number: 74–90.
*Length.*—About 6 mm.
*Width.*—At apex: About 2–3 mm. At base: About 1–2 mm.
*Disc area diameter.*—About 15 mm.
*Overall shape.*—Tubular.
*Shape at apex.*—Star with 5 triangular tips.
*Shape at base.*—Fused to tube.
*Margin.*—Entire.
*Texture.*—Glabrous.
*Color (when opening).*—Upper and under side: Gray-purple, RHS 186A (tip); light purple, RHS 76D (base).
*Color (fully opened).*—Upper and under side: Gray-orange, RHS 166A (tip); basal tube light gray-orange, RHS 162D.

Phyllaries:
*Quantity per inflorescence.*—About 30 in 1½ whorl.
*Length.*—About 10–16 mm.
*Width.*—About 1–3 mm.
*Overall shape.*—Lanceolate.
*Shape at apex.*—Acuminate.
*Shape at base.*—Fused.
*Margin.*—Entire.
*Texture.*—Upper surface: Smooth. Lower surface: Smooth.
*Color.*—Upper surface: RHS 143D, green, with translucent edges. Lower surface: RHS 141A, green.

Reproductive organs:
Androecium: On disc florets only.
*Stamen number.*—5 per floret; fused around style.
*Stamen length.*—About 2 mm.
*Anther shape.*—Linear.
*Anther length.*—About 1 mm.
*Anther color.*—RHS 176A, gray-orange.
*Pollen amount.*—Plenty.
*Pollen color.*—RHS N25A, Orange.

Gynoecium: On ray and disc florets.
*Quantity.*—1 per floret.
*Pistil length.*—About 4 mm.
*Stigma shape.*—Brush-like.
*Stigma color.*—Purple.
*Style length.*—About 2 mm.
*Style color.*—RHS 155B, White.
*Ovary color.*—RHS 2D, green-yellow.

Seed: None observed at this stage of development.
Fruit: None observed.
Disease/pest resistance: Good.

Disease/pest susceptibility: Low.

Temperature tolerance: Plants of the new *Osteospermum* have exhibited good tolerance to draught, rain and wind; however, flowering may cease during hot periods (night temperatures above 25° C.). Low temperature tolerance to 1° C.

Growth retardant(s): 3 times 0.2% Chlormequat drench during production.

I claim:

1. A new and distinct cultivar of *Osteospermum* plant named 'Sunny Florence', as illustrated and described herein.

* * * * *